C. F. GLOYSTEIN.
MANUFACTURE OF CONCENTRATED TOBACCO EXTRACT.
APPLICATION FILED MAY 25, 1909.
Reissued July 27, 1909. 12,994.
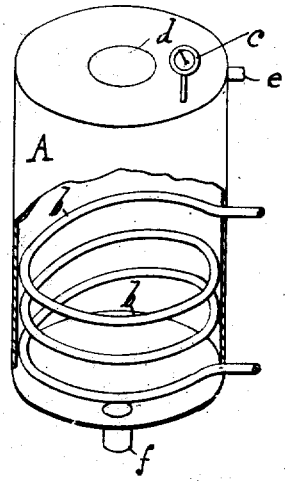
WITNESSES
L. H. Grote
M. E. Keir
INVENTOR
Christian Friedrich Gloystein
BY
Howson and Howson
ATTORNEYS

UNITED STATES PATENT OFFICE.

CHRISTIAN FRIEDRICH GLOYSTEIN, OF HENDERSON, KENTUCKY.

MANUFACTURE OF CONCENTRATED TOBACCO EXTRACT.

No. 12,994. Specification of Reissued Letters Patent. Reissued July 27, 1909.

Original No. 899,865, dated September 29, 1908, Serial No. 410,210. Application for reissue filed May 25, 1909. Serial No. 498,382.

*To all whom it may concern:*

Be it known that I, CHRISTIAN FRIEDRICH GLOYSTEIN, a subject of the German Empire, residing at Henderson, in the county of Henderson and State of Kentucky, have invented a new and useful Improvement in the Manufacture of Concentrated Tobacco Extracts, of which the following is a specification.

The invention consists of an improved method of treating raw aqueous tobacco-extract, whereby I obtain an extract free from sediment.

Raw aqueous tobacco extract usually contains in addition to suspended dirt, incident to the process of obtaining the extract, a certain quantity of albumen, which when the extract is concentrated forms an undesirable precipitate. I have discovered that this precipitation may be readily avoided by a preliminary treatment which has the effect of permanently converting part of the albumens into peptones and precipitating the remainder so that the latter may be extracted by filtration.

The method in its preferred form consists in heating the raw aqueous tobacco extract to a temperature above 100° C. and under pressure until the albumens have been precipitated or transformed into peptones. I have found that if the temperature be raised to about 160° C. and the pressure be kept at about 100 pounds to the square inch, this process is complete in about an hour. The same result may be obtained although the temperature and pressure be varied provided the temperature be kept above 100° C.

In the accompanying drawing is shown in side elevation partly broken away, a simple apparatus for carrying out the process.

A strong tank A, preferably made of steel is provided with heating coils, *b*, of copper or brass, a gage *c*, a man-hole *d*, and convenient inlets and outlets for the extract, *e* and *f* respectively.

The tank, A, is filled to one-half or three-fourths of its capacity with raw aqueous tobacco extract. Then steam of sufficient pressure is applied to the heating coil, *b*, until the tobacco extract has reached the temperature of about 160° C. and there is a pressure of about 100 pounds to the square inch on the tank, which will be shown by the gage, *c*. The heat and pressure is now kept constant for about an hour. After the steam is cut off and the tobacco extract sufficiently cooled down, the extract can be drawn off and filtered, to be cleaned of its suspended dirt and precipitated albumen and then concentrated.

I claim as my invention:

1. The process of treating tobacco extract which consists in subjecting the same to a temperature above its boiling point under pressure and subsequently filtering the same whereby the albumens present are either permanently converted into peptones or precipitated and removed and a permanently clear extract produced, as described.

2. The process of treating tobacco extract which consists in subjecting the same to a temperature of approximately 160° under 100 pounds pressure and subsequently filtering whereby the albumens present are either permanently converted into pe tones or precipitated and removed and a permanently clear extract produced, as described.

3. The process of treating tobacco extract which consists in subjecting the raw aqueous extract to a temperature above its boiling point under pressure, then filtering and concentrating the same whereby a concentrated extract permanently free of sediment is obtained.

4. As a new product, a tobacco extract permanently free from sediment, having portion of its normal albumens transformed into peptones and the remainder extracted by precipitation, substantially as described.

In testimony whereof I have signed my name to this specification in the presence of two subscribing witnesses.

CHRISTIAN FRIEDRICH GLOYSTEIN.

Witnesses:
A. L. MEADER,
C. TOLLNERS.